(12) United States Patent
Ritter et al.

(10) Patent No.: US 7,083,709 B2
(45) Date of Patent: Aug. 1, 2006

(54) POTENTIOMETRIC, ION-SELECTIVE ELECTRODE

(75) Inventors: Christoph Ritter, Graz (AT); Christian Neuhold, Graz (AT); Ursula Spichiger, Au (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/841,795

(22) Filed: May 7, 2004

(65) Prior Publication Data

US 2005/0000803 A1 Jan. 6, 2005

(30) Foreign Application Priority Data

May 15, 2003 (AT) .............................. A 744/2003

(51) Int. Cl.
*G01N 27/333* (2006.01)
(52) U.S. Cl. ...................................... 204/418; 204/416
(58) Field of Classification Search ......... 204/416–418
See application file for complete search history.

(56) References Cited

U.S. PATENT DOCUMENTS

| | | | |
|---|---|---|---|
| 3,926,764 A | 12/1975 | Ruzicka et al. | |
| 5,395,505 A | 3/1995 | Band et al. | |
| 5,804,049 A | 9/1998 | Chan | 204/418 |
| 5,840,168 A | 11/1998 | Chaniotakis et al. | 204/416 |
| 5,897,758 A | 4/1999 | Musacchio et al. | 204/418 |

FOREIGN PATENT DOCUMENTS

| | | |
|---|---|---|
| CH | 677295 A5 | 4/1991 |
| JP | 56066747 A | 6/1981 |
| SU | 1418608 A1 | 8/1988 |
| WO | WO 01/65247 A1 | 9/2001 |

OTHER PUBLICATIONS

Entries beryllium, barium, strontium, and radium in Hawley's Condensed Chemical Dictionary, 14th Edition.*
Pp. 164, 165, 448, 449, 169, 170, 528, 529, 516, 517 of the Handbook of Inorganic Chemicals, Pradyot Patnaik, McGraw-Hill, 2003.*
Derwent abstract of DD 256210A (Meierhofer et al.).*
Durselen, L.F.J., Oesterle, U., Schuppisser, S., Pham, H.V., Miyahara, Y., Morf, W.E., Simon, W. "New Solid-State Contact for Ion-Selective Liquid Membrane Electrodes", Chimia 44 (1990), Nr. 6, 214-215.

* cited by examiner

*Primary Examiner*—Alex Noguerola

(57) ABSTRACT

The invention relates to a potentiometric, ion-selective electrode for the measurement of cation concentration in a sample, which electrode is made of electrically conductive electrode material applied on an electrically insulating substrate using a thick-film technique and covered in the measurement area by an ion-sensitive membrane, preferably a liquid polymeric membrane. At least one water-soluble alkaline-earth metal salt is homogeneously dispersed in the electrode material. The water solubility of the alkaline-earth metal salt is preferably greater than $1\times10^{-2}$ µ/l, and lies preferably between $1\times10^{-2}$ and $1\times10^{-1}$ g/l.

10 Claims, 1 Drawing Sheet

POTENTIOMETRIC, ION-SELECTIVE ELECTRODE

PRIORITY CLAIM

The application claims priority under 35 U.S.C. §119 to Austrian Application No. A 744/2003 filed May 15, 2003.

BACKGROUND OF THE INVENTION

The invention relates to a potentiometric, ion-selective electrode for measuring the cation concentration in a sample, which electrode is made of electrically conductive electrode material applied on an electrically insulating substrate using a thick-film technique and covered in the measurement area by an ion-sensitive membrane, preferably a liquid polymeric membrane.

The use of ion-sensitive electrodes (ISEs) for determination of the concentration or the activity of ions in aqueous media has been known for a long time. Conventional ISEs generally consist of an ion-sensitive membrane, which has at least one ion-sensitive component, and is placed in a plastic housing in such a way that one side of the membrane is contacted by the sample whose concentration or activity is to be determined, while the other side is in contact with an aqueous solution of precisely defined concentration, i.e. the so-called internal electrolyte. The presence of the internal electrolyte is characteristic for this type of electrode; its constant composition together with the integrated internal reference system (usually Ag/AgCl) will guarantee stable potentials and thus accurate and reliable measurements of concentration or activity. A detailed description of the structure and function of ion-sensitive electrodes can be found in "Chemical Sensors and Biosensors for Medical and Biological Applications", Wiley-VCH, 1998, for example. On page 161 of this publication the structure and function of a liquid polymeric membrane is described. ISEs of this conventional type suffer from the disadvantage that, due to the aqueous component (i.e., the internal electrolyte), they are failure-prone, costly, difficult to manufacture, and that the possibilities for miniaturization are limited.

DESCRIPTION OF PRIOR ART

A conventional ion-selective electrode for calcium configured as a solid state electrode, predominantly made from calcium fluoride and a small quantity of another fluoride, for instance lanthanum fluoride, is known from JP 56-066747 A. The electrode has a cylindrical housing provided with an aqueous solution as an internal electrolyte, in which an Ag/AgCl reference electrode is immersed.

From SU 1418608 A an Mg-selective membrane electrode is known, whose membrane is applied on a small PVC tube with a diameter of 10 mm, which is filled with an internal electrolyte. During manufacture of the membrane a magnesium salt is added to a mixture of an ionophore (diphenyl-phenantroline) and borate (sodium tetraphenyl borate). The electrode is suitable for the measuring of magnesium in medical and pharmaceutical applications.

In the past few years ion-sensitive electrodes have been developed whose aqueous internal electrolyte has been replaced by a solid contact. In these solid-contact electrodes the liquid polymeric membrane is placed directly on the electrically conductive electrode material (a conductor or semi-conductor). Such systems permit extreme miniaturization of sensors. Their chief disadvantage lies in their unstable potential, which is due to the electrical or electrochemical resistance of the boundary surface between the region of electronic conductivity of the electrode and the region of conductivity by ionic movement of the ion-sensitive membrane.

A number of papers have described solutions of this problem of unstable potential through the use of redox couples, either in an interface layer between electrically conductive electrode material and ion-sensitive membrane, or directly added to the ion-sensitive membrane. In CH 677295 A5 and in Chimia 44, 1990, 214–215, a description is given of the possibility to reduce the boundary surface resistance between the electrical contact and the ion-sensitive membrane by adding a redox couple (generally halogen/halide) either as an interface layer or by vapor-deposition on the contact material. This method suffers from the disadvantage of relatively high manufacturing costs (vapour-deposition on the surface) and of a very long conditioning phase of the membrane, taking up to three days.

U.S. Pat. No. 5,804,049 A describes a so-called fortiophore material used for potential stabilisation. This is a polymeric material which is able to form stable, reproducible boundary surfaces between the ionic and the electronic regions of an ion-sensitive sensor. This polymeric material is preferably applied between the internal reference element and the ion-sensitive membrane. It preferably consists of a copolymer of methacryl-amidopropyl-trimethylammonium chloride and methyl-methacrylat. In this case it is of disadvantage that an interface layer between the electrical contact and the ion-selective membrane is used, which will increase manufacturing expense, and that adherence problems may arise due to aqueous swelling which eventually may lead to the destruction of the composite membrane element.

According to U.S. Pat. No. 5,897,758 A a fortiophore consists of a neutral complexing agent, for instance dodecyl-16-crown-5-ether, combined with a silver salt, such as silver nitrate, silver benzoate or others, which are directly added to the ion-selective membrane (e.g. for potassium with valinomycin as the ion-selective component). Potential stabilisation is achieved by complex-formation with the conductive ion of the electrical conductor, e.g. silver, which results in a defined junction between ionic and electronic domains of the sensor.

Potential stability is also appreciably improved during the wet-up phase and also over a longer period of time by adding a lipophilic silver ligand complex and the free ligand directly to the polymeric membrane of ion-sensitive electrodes for the determination of sodium or ammonium (Anal. Chim. Acta 321, 1996, 173–183). The silver ligand complex and the free ligand act as a potential-stabilising reversible redox couple at the boundary surface of the polymeric membrane and the silver contact.

In U.S. Pat. No. 5,840,168 A potential stabilisation for a solid-contact ion-selective electrode is achieved by fixing the M/MX-ratio (preferably Ag/AgCl) by adding large amounts of X-salts (e.g. KCl) to the substrate, a porous graphite rod. The graphite rod is loaded with the salt by immersing it for several hours in a mixture of salt, ionophore and plasticizer in THF. The high concentration of the salt prevents changes in the Ag/AgCl-ratio, thus achieving a stable potential situation.

WO 01/65247 A1 describes to use of an interface layer of sodium-vanadium-bronze, which also stabilises the junction between ion-selective membrane and electrical contact.

A grave disadvantage of all of these systems are high manufacturing costs. Application of an interface layer requires an additional step in the manufacturing process. Furthermore all interface layers are prone to a certain degree of swelling, which may cause adherence problems and may eventually lead to detachment of the ion-selective membrane. In addition, systems containing a redox couple are themselves sensitive against redox-active substances which might be present in a sample.

SUMMARY OF THE INVENTION

It is the object of the present invention to propose a miniaturizable, potentiometric, ion-selective electrode for measuring the concentration of a cation in a sample, which has an appreciably enhanced potential stability and an improved or at least not reduced sensitivity to the ion to be measured. Manufacture of the electrode should be reasonably simple and low-cost, employing the principles of thick-film technology.

According to the invention this object is achieved by providing that at least one water-soluble salt of an alkaline-earth metal should be homogeneously distributed in the electrode material. The alkaline-earth metal salt of the form $M_mX_n$ is suspensible in the matrix of the electrode material. The aqueous solubility of the alkaline-earth metal salt is preferably greater than $1\times10^{-2}$ g/l, and lies for instance between $1\times10^{-2}$ g/l and $1\times10^{-1}$ g/l.

According to the invention the electrode material may contain finely dispersed activated carbon-, carbon-, graphite-, or metal particles, and 10 to 40, preferably 20 to 30, percent by weight, of at least one alkaline-earth metal salt.

For the electrode all known materials suitable for thick-film technology may be used, provided an admixture of an alkaline-earth metal salt is possible. As a base material finely distributed metal particles in an organic substrate (EP 0 444 840 A1) are suitable, which particles might also contain non-metallic substances (U.S. Pat. No. 5,897,758).

For the measurement of $Mg^{2+}$— or $Ca^{2+}$— concentration in a sample the electrode material of the ion-sensitive electrode will contain the chloride of the cation to be measured, according to a preferred variant of the invention The electrode material is for instance manufactured by working finely pulverized $MgCl_2$, and a graphite paste, consisting of graphite or activated carbon particles, and a polymer binding agent into a paste, in which, after evaporation of the solvent, the magnesium salt is homogeneously dispersed in the whole matrix.

For the measurement of $Mg^{2+}$— or $Ca^{2+}$— concentration in a sample, it will further be possible according to the invention that the electrode material contains the acetate of the cation to be measured.

In certain cases an enhancement of the selectivity of the electrode occurs as a side-effect of adding the salt of an alkaline-earth metal to the electrode material (e.g. in the case of an ion-selective sensor for determination of the concentration of magnesium ions in physiological fluids).

The manufacture of an ion-selective magnesium electrode as proposed by the invention using magnesium chloride as a redox-inactive salt will now be described in more detail.

EXAMPLE

Preparation of the Electrically Conductive Electrode Material 20 to 30 parts by weight of magnesium chloride are mixed with 70 to 80 parts by weight graphite paste (for instance Elektrodag 421 SS of Acheson Colloiden B.V. Scheenda/Netherlands) and processed into a homogeneous paste in a mortar.

Preparation of the Electrode

The electrically conductive electrode material is applied onto a polycarbonate plate in the shape of a rectangle by means of a screen-printing process, and the free surfaces are coated with an insulating varnish, excepting two areas, i.e. one area for the contact of the electronic amplifier and one area where the ion-selective membrane is to be applied. Pastes of the type described are very suitable for screen-printing on account of the fine pulverization of the salt.

For the purpose of comparison unmodified electrodes were produced as well; in that case the unmodified electrode material (for instance Elektrodag 421 SS of Acheson Colloiden B.V. Scheenda/Netherlands) without the addition of the alkaline-earth metal salt was applied onto a polycarbonate plate in the shape of a rectangle by means of a screen-printing process, and the free surfaces were covered with an insulating varnish, excepting the area for the contact of the electronic amplifier and the area where the ion-selective membrane is to be applied.

Finally, an ion-selective membrane, consisting of a solution of 60–70% plasticizer, 30–40% PVC, 0–2% borate and 1–3% ionophore in THF, is applied onto the free surface of the measurement area After the solvent has evaporated the sensors are ready for use.

Measurements

Measurement of the individual parameters was carried out potentiometrically; a calomel electrode was used as a reference electrode. Standard solutions of Roche Diagnostics GmbH were used as test media The potential was measured as a function of the composition of the individual standard solutions and as a function of the time elapsed after initial contact of the electrode with the standard solution. The concentration of primary ions and interfering ions was systematically varied.

Further features and advantages of the invention will become apparent from the following discussion and the accompanying drawings in which:

BRIEF DESCRIPTION OF THE DRAWINGS

The invention will be further described below with reference to the enclosed drawings, wherein.

DETAILED DESCRIPTION

The following description of the preferred embodiment is merely exemplary in nature and is in no way intended to limit the invention or its application or uses.

Figure 1:
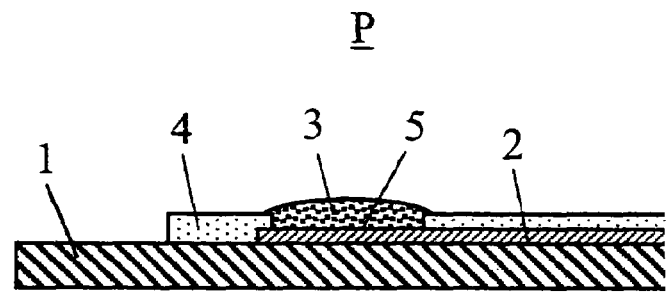
FIG. 1 is a schematic sectional view of an ion-selective electrode according to the invention.

As can be seen in FIG. 1, the electrically conductive electrode material 2 containing the salt of an alkaline-earth metal is applied on an electrically insulating substrate 1, consisting for instance of polycarbonate, and in the measurement area 5 the ion-selective membrane 3 is applied on the electrode. An insulating layer 4 seals the electrode material 2 against direct contact with the sample P. The electrode material 2 and the insulating layer 4 are preferably applied by means of a screen-printing process.

The electrode material 2 consists of graphite or activated carbon particles and particles of the alkaline-earth metal salt. The individual particles are bound by a binding agent.

Figure 2:
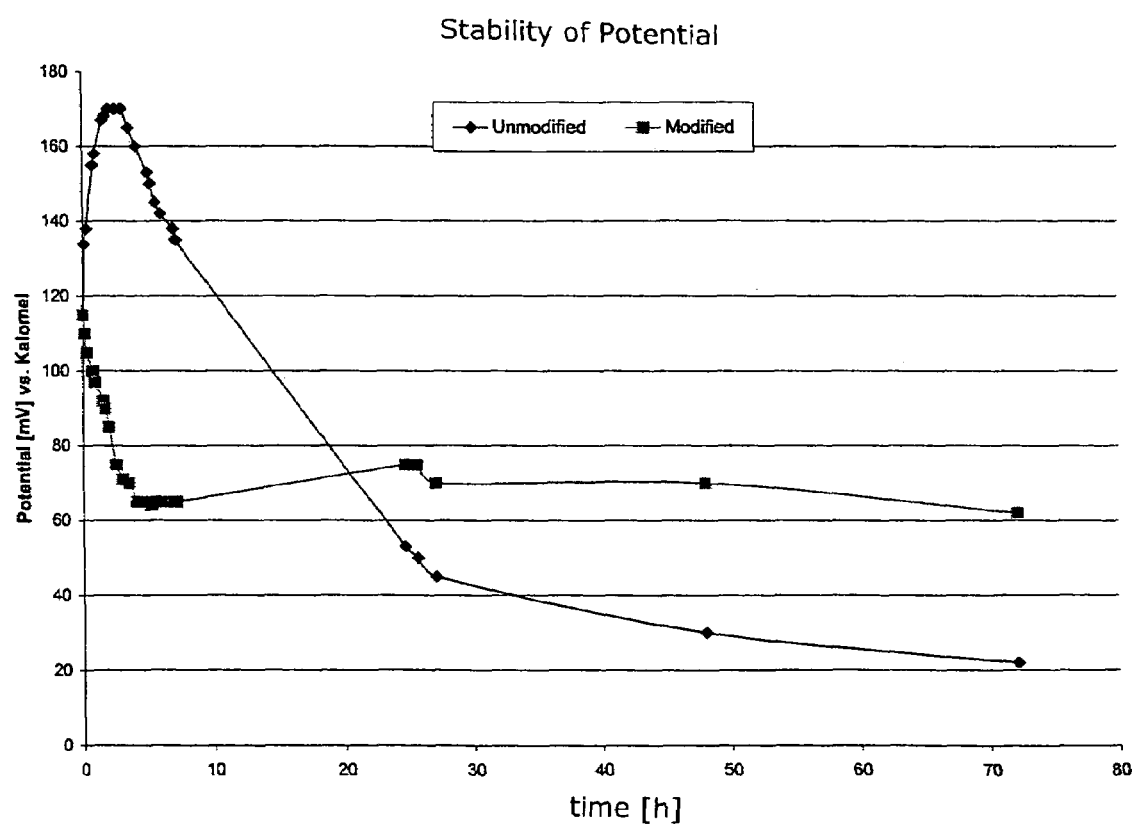
FIG. 2 is a diagram of measurements obtained with the ion-selective electrode of the invention.

FIG. 2 shows the potential of an ion-selective electrode according to the invention as a function of the time elapsed after initial contact of the electrode with the standard solution in comparison with the potential of a conventional electrode without the addition of an alkaline-earth metal salt.

As can be seen from FIG. 2, ion-selective electrodes containing an alkaline-earth metal salt in the electrode material (marked "modified"), exhibit, after an initial stabilizing phase, a more stable behavior and above all a considerably smaller potential drift than conventional electrodes. After a stabilizing phase of approx. 3 hours after initial contact of the electrode with the standard solution, the potential against a reference electrode will thus change very little over a period of some days, as compared with a conventional electrode (marked "unmodified").

A side-effect of the addition of an alkaline-earth metal salt to the electrode material is an enhancement of the selectivity of the electrode, as for instance in the case of an ion-selective electrode for the measurement of magnesium in body fluids. The following table shows the influence of the presence of magnesium salt in the electrode material on the selectivity of electrodes in accordance with the invention as compared to electrodes having no salt in the electrode material.

| Time [h] | Unmodified Spots | Modified Spots |
|---|---|---|
| Sensitivity of the Mg-Sensor to Mg [mV/decade] | | |
| 0.5 | 13.3 | 15.8 |
| 3 | 13.0 | 15.1 |
| 24 | 9.6 | 13.3 |
| 48 | 9.6 | 13.4 |
| Sensitivity of the Mg-Sensor to Ca [mV/decade] | | |
| 0.5 | 15.7 | 15.7 |
| 3 | 17.2 | 16.7 |
| 24 | 17.7 | 16.4 |
| 48 | 18.8 | 17.7 |

The addition of the magnesium salt to the material of the electrode has improved the sensitivity of the electrode to magnesium (higher values), while the influence of calcium was slightly reduced (lower values). The improved sensitivity behavior is upheld over the whole lifetime of the electrode. This improvement of Mg-sensitivity, which has also been observed in classical ion-selective electrodes (electrodes with internal electrolyte) for the determination of magnesium (e.g. Eugster, Spichiger, Simon, Anal. Chem. 65, 1993, pp. 689–695) admits the interpretation that in the instance of an electrode according to the invention a ionophore gradient will arise within the membrane directed towards the outside of the membrane (lower concentration of the ionophore), which due to the differing stoichiometry of the ion-ionophore complex for Mg (1:1) and Ca (1:2) will result in prevalent complexing of the Mg-ion when the ionophore is depleted at the outer side of the membrane. This effect is not only observed when the concentration of magnesium ions at the inner side of the membrane of the ion-selective sensor is high, but also when there is a high concentration of calcium ions at the inner side of the membrane of the ion-selective sensor.

As any person skilled in the art will recognize from the previous description and from the figures and claims, modifications and changes can be made to the preferred embodiment of the invention without departing from the scope of the invention as defined in the following claims.

What we claim is:

1. A potentiometric, ion-selective electrode for measuring the concentration of a cation in a sample, comprising an electrically conductive electrode material applied on an electrically insulating substrate using a thick-film technique and covered in a measurement area by an ion-sensitive membrane, wherein at least one water-soluble alkaline-earth metal salt is homogeneously dispersed in said electrode material.

2. The electrode of claim 1, wherein water solubility of said alkaline-earth metal salt is greater than $1 \times 10^{-2}$ g/l.

3. The electrode of claim 2, wherein water solubility of said alkaline-earth metal salt lies between $1 \times 10^{-2}$ and $1 \times 10^{-1}$ g/l.

4. The electrode of claim 1, wherein said electrode material contains finely dispersed activated carbon-, carbon-, graphite-, or metal particles and 10 to 40 percent by weight of said at least one alkaline-earth metal salt.

5. The electrode of claim 4, wherein said electrode material contains 20 to 30 percent by weight of said at least one alkaline-earth metal salt.

6. The electrode of claim 1 for measuring $Mg^{2+}$— concentrations in a sample, wherein said electrode material contains a chloride of the cation to be measured.

7. The electrode of claim 1 for measuring $Ca^{2+}$— concentrations in a sample, wherein said electrode material contains a chloride of the cation to be measured.

8. The electrode of claim 1 for measuring the $Mg^{2+}$— concentrations in a sample, wherein said electrode material contains an acetate of the cation to be measured.

9. The electrode of claim 1 for measuring the $Ca^{2+}$— concentrations in a sample, wherein said electrode material contains an acetate of the cation to be measured.

10. The electrode of claim 1, wherein said ion-sensitive membrane is a liquid polymeric membrane.

* * * * *